United States Patent [19]

Hamill et al.

[11] 4,331,658
[45] May 25, 1982

[54] METHOD OF TREATING SWINE DYSENTERY WITH ANTIBIOTIC A-32887

[75] Inventors: Robert L. Hamill, Greenwood; Marvin M. Hoehn, Indianapolis, both of Ind.

[73] Assignee: Eli Lilly and Company, Indianapolis, Ind.

[21] Appl. No.: 123,852

[22] Filed: Feb. 22, 1980

Related U.S. Application Data

[60] Continuation-in-part of Ser. No. 12,182, Feb. 14, 1979, abandoned, which is a continuation-in-part of Ser. No. 838,524, Oct. 3, 1977, abandoned, which is a division of Ser. No. 801,876, May 31, 1977, Pat. No. 4,133,876.

[51] Int. Cl.$^3$ .................... A61K 35/00; A61K 31/35
[52] U.S. Cl. .................... 424/121; 424/122; 424/283
[58] Field of Search .................... 424/283, 121, 122

[56] References Cited

PUBLICATIONS

Tsuji et al., J. Antibiotics, 29, pp. 10–14 (1976).

*Primary Examiner*—Jerome D. Goldberg
*Attorney, Agent, or Firm*—Nancy J. Harrison; Arthur R. Whale

[57] ABSTRACT

Method and compositions for treatment of swine dysentery with antibiotic A-32887 (K-41). Antibiotic A-32887 is produced by submerged aerobic fermentation of *Streptomyces albus* NRRL 11109.

9 Claims, 6 Drawing Figures

FIG. I

METHOD OF TREATING SWINE DYSENTERY WITH ANTIBIOTIC A-32887

CROSS-REFERENCES TO RELATED APPLICATIONS

This is a continuation-in-part application of our copending application Ser. No. 12,182, filed Feb. 14, 1979, now abandoned, which in turn is a continuation-in-part application of application Ser. No. 838,524, filed Oct. 3, 1977, now abandoned, which in turn is a division of application Ser. No. 801,876, filed May 31, 1977, now issued U.S. Pat. No. 4,133,876.

BACKGROUND OF THE INVENTION

1. Field of the Invention

New, improved antibiotics are continually in demand. In addition to antibiotics which are useful for human diseases, improved antibiotics are also needed in the veterinary field.

Swine dysentery is a common disease of swine in the United States. It causes great economic losses. The disease is very contagious and can be highly destructive. It is frequently desirable, therefore, to treat even healthy herds which are threatened by outbreaks of the disease.

2. The Prior Art

A-32887 is a polyether antibiotic. At the time parent application Ser. No. 801,876 was filed, A-32887 was thought to be closely related to, but different from, the prior art antibiotic K-41 [*J. Antibiotics* 29 (1), 10–14 (1976)]. Subsequently, however, it has been determined that A-32887 is identical to K-41. A-32887 (K-41) has the following structure:

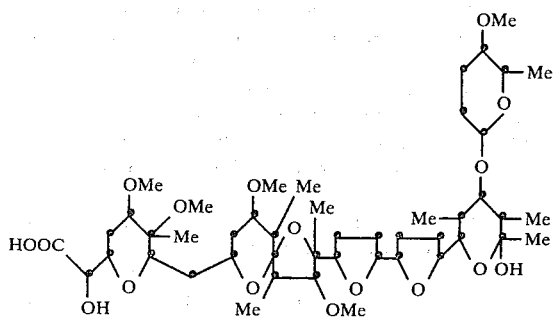

K-41 was known to be useful as a Gram-positive antibiotic. The fact that K-41 is useful for the treatment of swine dysentery, however, was not previously recognized.

SUMMARY OF THE INVENTION

This invention relates to an antibiotic substance which is produced by culturing the organism *Streptomyces albus* NRRL 11109.

The antibiotic substance of this invention is arbitrarily designated herein as A-32887. The $C_2$–$C_6$-acyl ester derivatives of antibiotic A-32887, the methyl ether derivative of antibiotic A-32887, and the pharmaceutically-acceptable salts of antibiotic A-32887 and of said ester and ether derivatives are also part of this invention. To simplify discussions of utility, the term "A-32887 compound" is used and refers to antibiotic A-32887, a specified acyl ester derivative of A-32887, the methyl ether derivative of A-32887 or a pharmaceutically-acceptable salt of A-32887 or of said ester or ether derivatives.

A-32887 is produced by culturing a novel strain of *Streptomyces albus,* NRRL 11109, under submerged aerobic fermentation conditions until a substantial level of antibiotic activity is produced. A-32887 is extracted from basified broth filtrate with polar organic solvents. The extracted A-32887 is purified by absorption chromatography.

A-32887 compounds are useful in the treatment of swine dysentery. In addition, A-32887 compounds are antibacterial, antifungal, anti-protozoal, anticoccidial, antiviral and insecticidal agents.

DESCRIPTION OF THE DRAWINGS

The following infrared absorption spectra in chloroform are presented in the drawings.

DETAILED DESCRIPTION

The following paragraphs describe the properties of antibiotic A-32887.

A-32887 is a white, amorphous powder which melts at approximately 90° C. Elemental analysis of A-32887 indicates that it has the following approximate percentage composition (average): Carbon, 61.61%; Hydrogen, 8.56%; Oxygen, 28.63%. A-32887 has an approximate empirical formula of $C_{48-49}H_{80-86}O_{17-18}$ and a preferred empirical formula of $C_{48}H_{82}O_{18}$.

A-32887 has a molecular weight of about 946, as determined by mass spectrometry.

Figure 1:
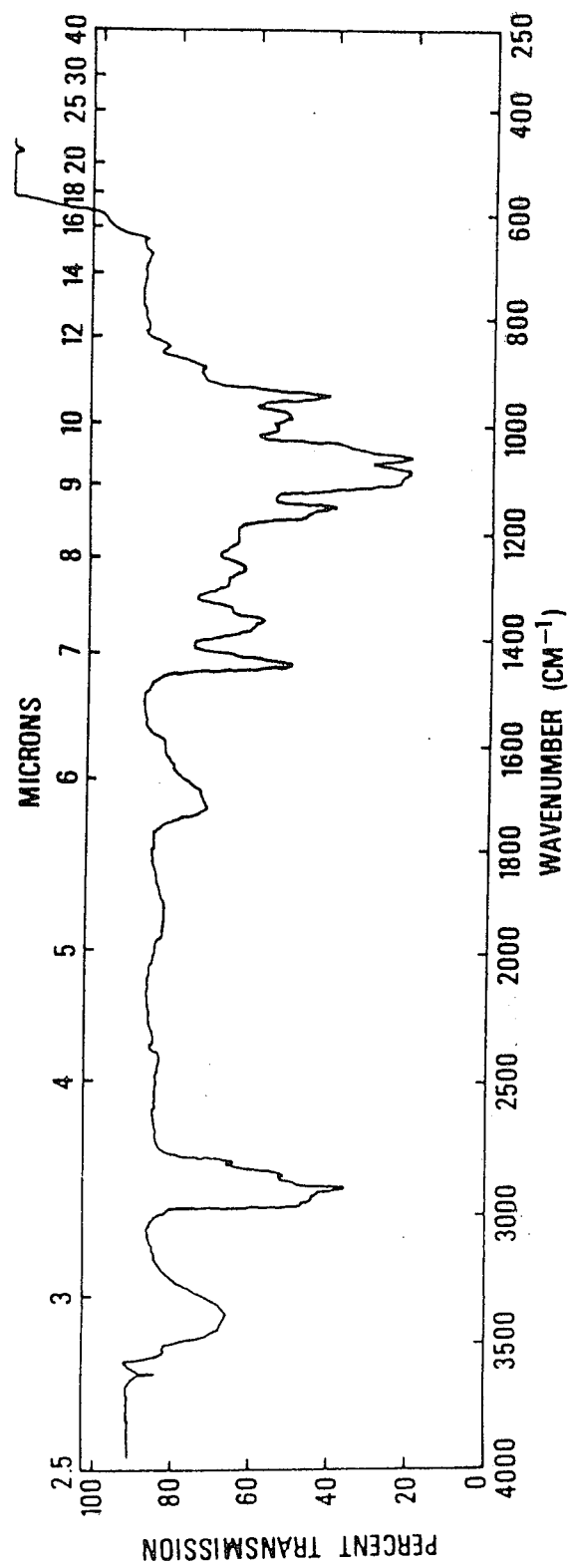
FIG. 1—A-32887 (free acid)
FIG. 2—A-32887 mixed sodium-potassium salt
FIG. 3—A-32887 sodium salt
FIG. 4—A-32887 acetyl ester derivative (Na-K salt)
FIG. 5—A-32887 n-butyryl ester derivative (Na-K salt)
FIG. 6—A-32887 methyl ether derivative (Na salt)

The infrared absorption spectrum of A-32887 (free acid) in chloroform is shown in FIG. 1 of the accompanying drawings. Significant absorption maxima occur at the following frequencies ($cm^{-1}$): 3540 (shoulder), 3420 (medium), 2945 (shoulder), 2905 (strong), 2860 (shoulder), 2805 (shoulder), 1710 (weak), 1450 (medium), 1370 (medium), 1350 (shoulder), 1300 (shoulder), 1275 (weak), 1170 (shoulder), 1155 (medium), 1100 (shoulder), 1085 (strong), 1060 (strong), 1010 (weak), 990 (weak), 980 (shoulder), 948 (medium), 890 (weak), and 850 (weak).

The ultraviolet spectrum of A-32887 shows no significant absorption.

The proton-magnetic-resonance spectrum of A-32887 indicates the presence of five methoxyl groups.

A-32887 (free acid) has the following specific rotation: $[\alpha]_D^{25} + 15.9°$ (c 1, $CHCl_3$).

A-32887 mixed sodium-potassium salt crystallizes from acetone-water and has a melting point of about 187°–190° C. Elemental analysis of A-32887 Na-K salt indicates that it has the following approximate percentage composition (average):
Carbon, 60.14; Hydrogen, 8.11%; Oxygen,
29.64%; Sodium, 2.31%; Potassium, 0.46%.

Figure 2:
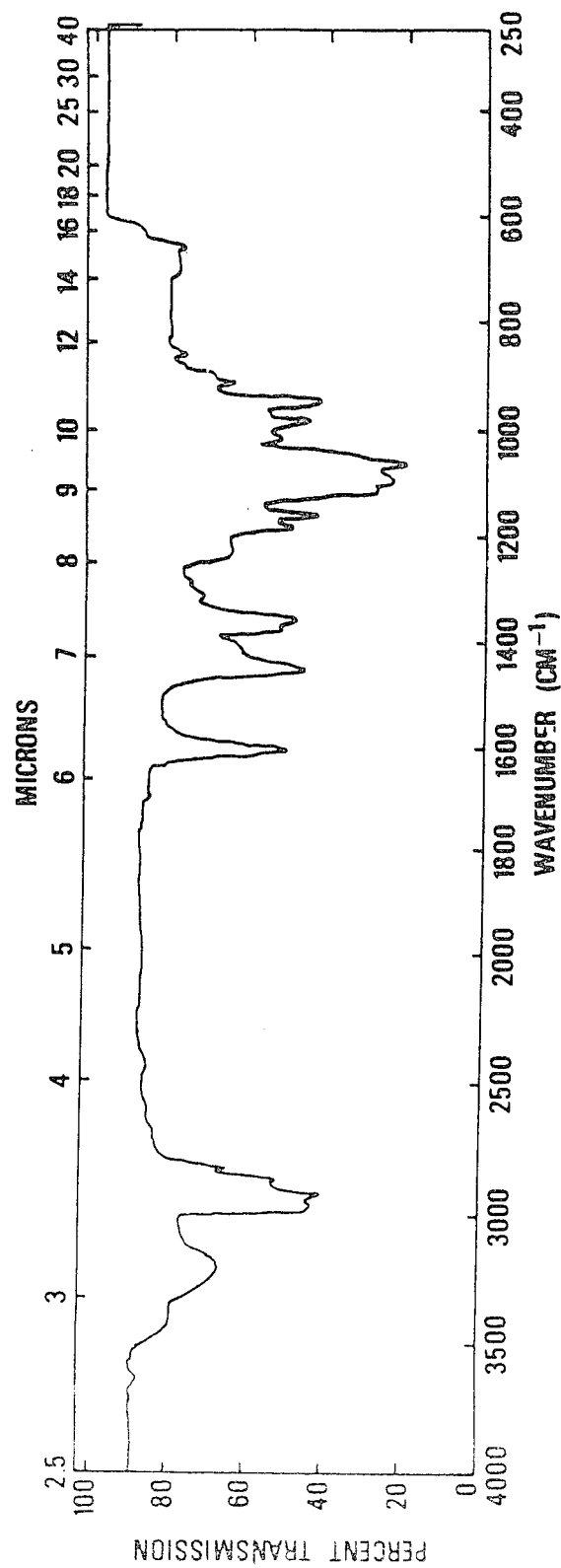
Figure 3:
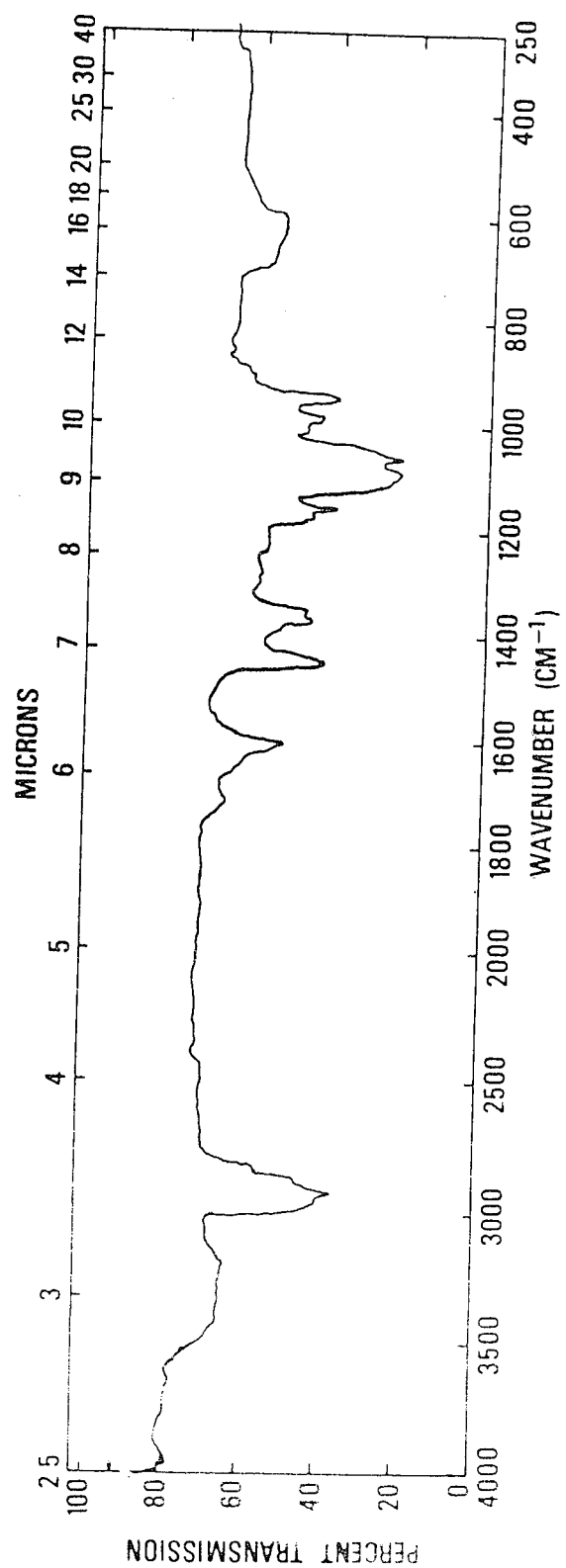

The infrared absorption spectrum of A-32887 Na-K salt in chloroform is shown in FIG. 2 of the accompanying drawings. Significant absorption maxima are observed at the following frequencies ($cm^{-1}$): 3400 (shoulder), 3210 (medium), 2970 (strong), 2925 (strong), 2870 (weak), 2820 (weak), 1605 (medium), 1455 (medium), 1375 (shoulder), 1358 (medium), 1310 (weak), 1285 (weak), 1183 (medium), 1160 (medium), 1110 (shoulder), 1090 (strong), 1060 (strong), 1012 (weak), 980 (medium), 942 (medium), 910 (weak), 875 (shoulder), and 858 (weak).

A-32887 Na-K salt, crystallized from acetone-water, has the following characteristic X-ray powder diffraction pattern (CuNi, 1.5405 λ, d=interplanar spacing in angstroms):

| d | Relative Intensity |
|---|---|
| 12.53 | 50 |
| 10.10 | 100 |
| 9.5 | 40 |
| 9.05 | 40 |
| 8.07 | 70 |
| 7.16 | 100 |
| 6.77 | 100 |
| 6.48 | 70 |
| 6.16 | 60 |
| 5.58 | 50 |
| 5.35 | 50 |
| 5.10 | 30 |
| 4.86 | 60 |
| 4.70 | 50 |
| 4.44 | 50 |
| 4.25 | 50 |
| 4.06 | 40 |
| 3.80 | 30 |
| 3.68 | 40 |
| 3.58 | 30 |
| 3.42 | 60 |
| 3.22 | 10 |
| 3.06 | 10 |
| 2.97 | 10 |
| 2.85 | 10 |
| 2.76 | 02 |
| 2.61 | 15 |
| 2.49 | 05 |
| 2.47 | 05 |
| 2.44 | 15 |
| 2.36 | 10 |
| 2.29 | 10 |
| 2.20 | 02 |
| 2.12 | 02 |
| 2.03 | 05 |
| 1.96 | 05 |
| 1.90 | 02 |
| 1.81 | 02 |

A-32887 Na-K salt has the following specific rotation:

$[\alpha]_D^{25} +9.6°$ (c 1, CHCl$_3$).

Electrometric titration of A-32887 in 80% aqueous dimethylformamide indicates the presence of a titratable group with a $pK_a$ value of 4.60.

A-32887 is soluble in a variety of organic solvents such as methanol, ethanol, dimethylformamide, dimethyl sulfoxide, ethyl acetate, chloroform, acetone, and benzene; is slightly soluble in non-polar organic solvents such as hexane and heptane; and is insoluble in water.

A-32887 is stable in aqueous solutions having a pH of from about 3 to about 11, but is unstable in solutions having a pH lower than about 3.

A-32887 sodium salt has a molecular weight of about 968, and A-32887 potassium salt has a molecular weight of about 984, both as determined by field-desorption (FD) mass spectrometry. The ion at m/e 969 (M+H) in the FD spectrum of A-32887 sodium salt was peak matched with a field-ionized mass standard. The found mass was 969.5373; the theoretical mass for $C_{48}H_{82}O_{18}Na$ is 969.5399. This finding supports a molecular formula of $C_{48}H_{82}O_{18}$ for A-32887 free acid.

In the following paper-chromatographic systems, using *Bacillus subtilis* ATCC 6633 bioautography for detection, A-32887 has these approximate $R_f$ values:

| Solvent System | $R_f$ Value |
|---|---|
| Water saturated with methyl isobutyl ketone (MIBK) | 0.58 |
| Water:methanol:acetone (12:3:1). This solution is adjusted to pH 10.5 with NH$_4$OH and then lowered to pH 7.5 with H$_3$PO$_4$ | 0.32 |
| Propanol:water (1:9) | 0.85 |
| Methanol:propanol:water (6:2:1). Paper buffered with 0.75 M KH$_2$PO$_4$, pH 4.0. | 0.79 |
| Methanol:0.05 M sodium citrate at pH 5.7 (7:3). Paper buffered with 0.05 M sodium citrate at pH 5.7. | 0.85 |
| Propanol:water (7:3) | 0.91 |

In the following silica-gel TLC systems, using either vanillin spray reagent or *Bacillus subtilis* ATCC 6633 bioautography for detection, A-32887 has the these approximate $R_f$ values:

| Solvent System | $R_f$ Value |
|---|---|
| Methanol | 0.80 |
| Ethyl acetate:ethanol (1:4) | 0.65 |
| Ethyl acetate:chloroform (1:1) | 0.36 |
| Ethyl acetate:chloroform (6:1) | 0.67 |
| Benzene:ethyl acetate:methanol (6:4:0.2) | 0.58 |

A-32887 has an acid function capable of forming salts and ester derivatives and has at least one hydroxyl group capable of esterification. The $C_2$–$C_6$-acyl ester derivatives of A-32887 and the pharmaceutically-acceptable salts of these ester derivatives are also useful in the treatment of swine dysentery.

The A-32887 acyl ester derivatives are typically prepared by reacting A-32887 with the corresponding $C_2$–$C_6$-acid anhydride or acid chloride at room temperature.

The following paragraphs describe characteristics of typical A-32887 acyl ester derivatives.

A-32887 acetyl ester derivative (Na-K salt) is a white amorphous powder which has a molecular weight of about 988 and a melting point of about 127°–129° C. A-32887 acetyl ester derivative has an approximate empirical formula of $C_{50-51}H_{82-88}O_{18-19}$.

Figure 4:
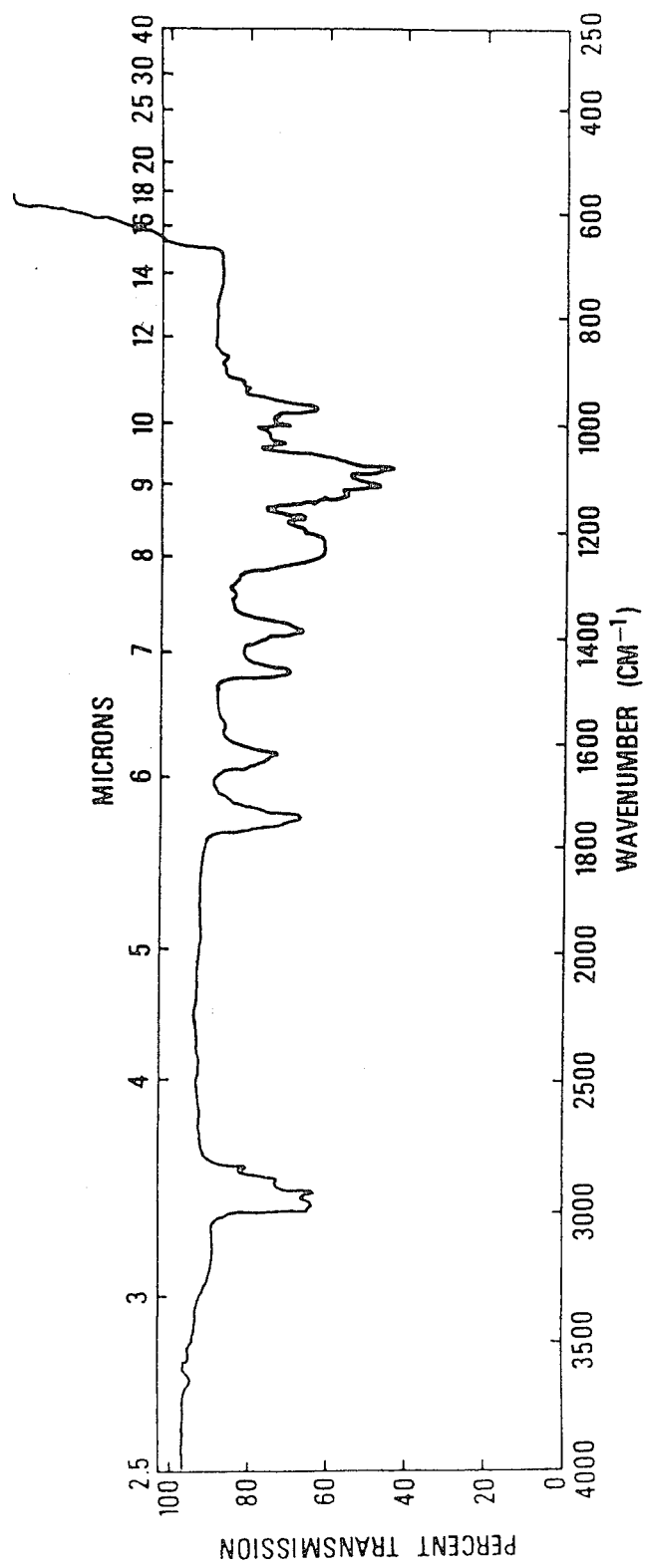

The infrared absorption spectrum of A-32887 acetyl ester derivative (Na-K salt) in chloroform is shown in FIG. 4 of the accompanying drawings. Significant absorption maxima occur at the following frequencies (cm$^{-1}$): 3000, 2975, 2932, 2875, 2830, 1733, 1634, 1620, 1610, 1453, 1372, 1305, 1158, 1110, 1092, 1062, 1014, 996, 978, 948, 909, 893, and 853.

A-32887 n-butyryl ester derivative (Na-K salt) is a white amorphous powder which has a molecular weight of about 1016 and a melting point of about 59°–62° C. A-32887 n-butyryl ester derivative has an approximate empirical formula of $C_{52-53}H_{86-92}O_{18-19}$.

Figure 5:
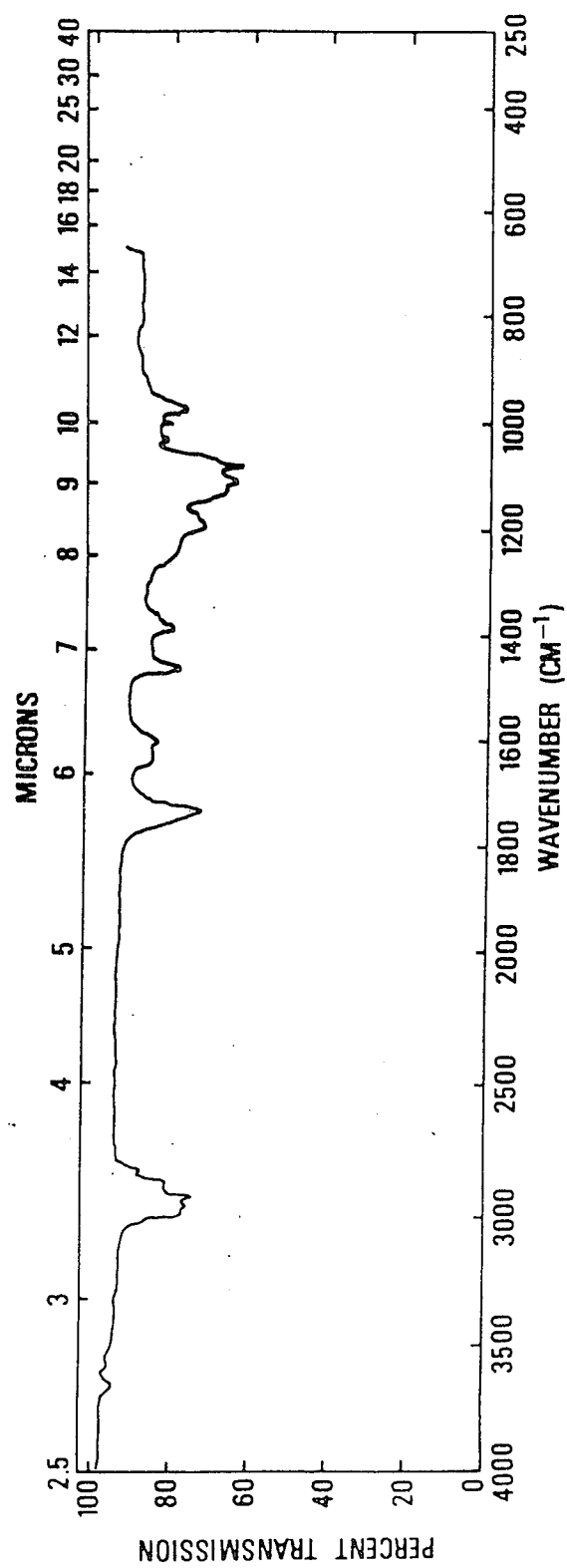

The infrared absorption spectrum of A-32887 n-butyryl ester derivative (Na-K salt) in chloroform is shown in FIG. 5 of the accompanying drawings. Significant absorption maxima occur at the following frequencies (cm$^{-1}$): 3000, 2968, 2932, 2875, 2830, 1724, 1630, 1620, 1610, 1592, 1452, 1372, 1355, 1179, 1155, 1110, 1090, 1060, 1012, 977, 946, and 892.

The $C_2$-$C_6$-acyl ester derivatives of A-32887 are soluble in a variety of organic solvents such as methanol, ethanol, dimethylformamide, dimethyl sulfoxide, ethyl acetate, chloroform, acetone, and benzene; are slightly soluble in non-polar organic solvents such as hexane and heptane, and are insoluble in water.

A-32887 can be distinguished from its $C_2$–$C_6$ acyl ester derivatives by TLC. For example, the acetyl and n-butyryl ester derivatives can be separated from A-32887 by silica-gel TLC using a benzene:ethyl acetate (1:1) solvent system. A sulfuric acid spray reagent can be used for detection. In this system A-32887 and its acetyl and n-butyryl ester derivatives have the following approximate $R_f$ values:

| | $R_f$ value |
|---|---|
| A-32887 (Na-K) | 0.47 |
| A-32887 acetyl ester derivative (Na-K) | 0.40 |
| A-32887 n-butyryl ester derivative (Na-K) | 0.64 |

The A-32887 hydroxyl group can react with lower alkanols, lower-alkyl thiols, and glycols to form ether derivatives using procedures similar to those described for the preparation of A204I derivatives in U.S. Pat. No. 3,907,832. The A-32887 $C_1$–$C_4$-alkyl ether derivatives and their pharmaceutically-acceptable salts are especially useful in this invention. Of the $C_1$–$C_4$-alkyl ether derivatives, the methyl ether derivative of A-32887 and its pharmaceutically-acceptable salts are preferred.

A-32887 methyl ether derivative has an approximate empirical formula of $C_{49-50}H_{82-88}O_{17-18}$. The sodium salt of A-32887 methyl ether derivative is a white crystalline (n-hexane:ethyl acetate) compound having a melting point of about 214°–216° C.

The molecular weight of A-32887 methyl ether derivative sodium salt is about 982; the molecular weight of A-32887 methyl ether derivative free acid is about 960 (both as determined by FD mass spectrometry).

Figure 6:
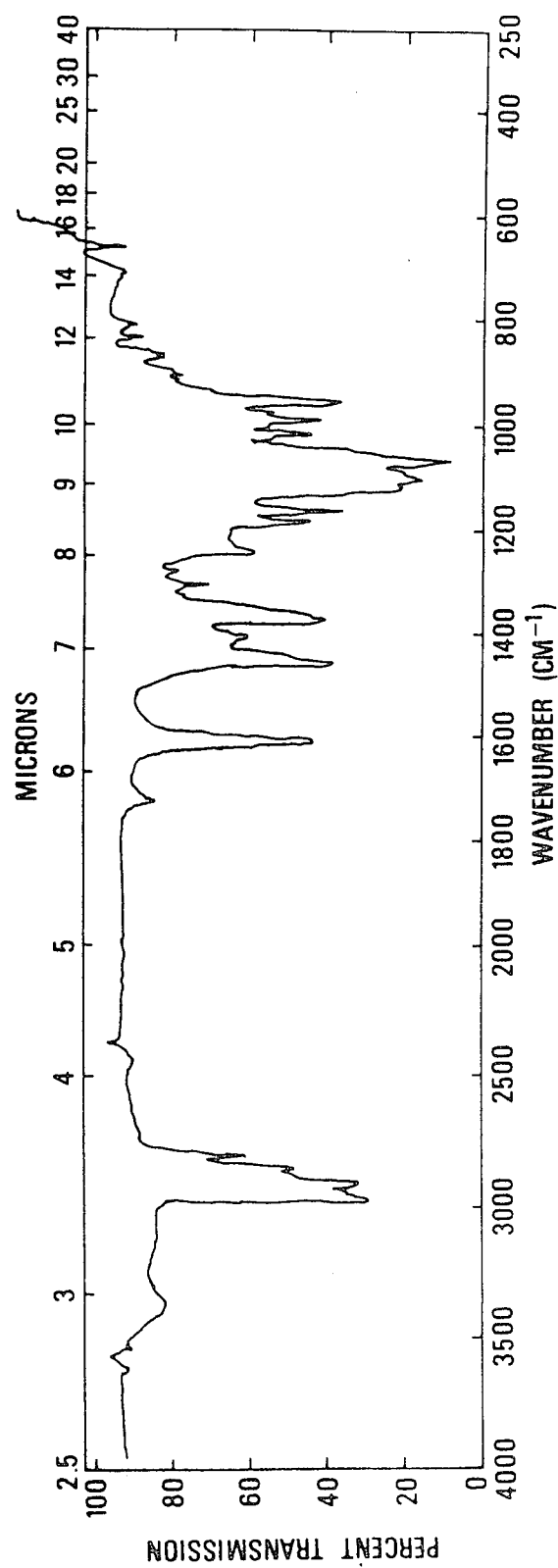

The infrared absorption spectrum of A-32887 methyl ether derivative (Na salt) in chloroform is shown in FIG. 6 of the accompanying drawings. Significant absorption maxima occur at the following frequencies (cm$^{-1}$): 3400 (broad), 2990, 2960, 2930, 2870, 2820, 1725, 1610, 1455, 1407, 1370, 1309, 1282, 1240, 1180, 1158, 1110, 1093, 1082, 1057, 1010, 980, 945, 900, 868, 858, 827, 802, 700, and 653.

The proton-magnetic-resonance spectrum of A-32887 methyl ether derivative (Na salt) indicates the presence of six methoxyl groups.

A-32887 methyl ether derivative (Na salt) has the following specific rotation: $[\alpha]_D^{25} - 5.1°$ (c 1, CHCl$_3$).

A-32887 methyl ether derivative (Na salt), crystallized from n-hexane:ethyl acetate, has the following characteristic X-ray powder diffraction pattern (CuNi, 1.5405 λ, d = interplanar spacing in angstroms):

| d | Relative Intensity |
|---|---|
| 13.18 | 50 |
| 12.01 | 50 |
| 9.02 | 100 |
| 8.26 | 100 |

-continued

| d | Relative Intensity |
|---|---|
| 7.19 | 80 |
| 6.46 | 50 |
| 5.78 | 20 |
| 5.46 | 20 |
| 5.00 | 30 |
| 4.24 | 20 |
| 3.72 | 20 |
| 3.36 | 05 |

Electrometric titration of A-32887 methyl ether derivative (Na salt) in 80% aqueous dimethylformamide indicates the presence of a titratable group with a pK$_a$ value of about 5.4.

A-32887 methyl ether derivative is soluble in a variety of organic solvents such as methanol, ethanol, dimethylformamide, dimethyl sulfoxide, ethyl acetate, chloroform, acetone, and benzene; is slightly soluble in non-polar organic solvents such as hexane and heptane; and is insoluble in water.

A-32887 methyl ether derivative (Na salt) can be separated from A-32887 (Na-K salt) by silica-gel TLC, using a benzene:ethyl acetate (1:1) solvent system and sulfuric acid spray reagent for detection. In this system, A-32887 and its methyl ether derivative have the following $R_f$ values:

| | $R_f$ Value |
|---|---|
| A-32887 (Na-K) | 0.425 |
| A-32887 methyl ether derivative (Na) | 0.22 |

A-32887, the $C_2$–$C_6$-acyl ester derivatives of A-32887, and A-32887 methyl ether derivative are capable of forming salts. The pharmaceutically-acceptable alkali-metal, alkaline-earth-metal and amine salts of A-32887, the $C_2$–$C_6$-acyl ester derivatives of A-32887, and A-32887 methyl ether derivative are also useful in the method of this invention. "Pharmaceutically-acceptable" salts are those in which the toxicity of the compound as a whole toward warm-blooded animals is not increased relative to the non-salt form. Representative and suitable alkali-metal and alkaline-earth metal salts of A-32887 include the sodium, potassium, lithium, cesium, rubidium, barium, calcium, and magnesium salts. Suitable amine salts of A-32887 include the ammonium and the primary, secondary, and tertiary $C_1$–$C_4$-alkylammonium and hydroxy-$C_2$–$C_4$-alkylammonium salts. Illustrative amine salts include those formed by reaction of A-32887 with ammonium hydroxide, methylamine, sec-butylamine, isopropylamine, diethylamine, di-isopropylamine, ethanolamine, triethylamine, 3-amino-1-propanol and the like.

The alkali-metal and alkaline-earth-metal cationic salts of A-32887 are prepared according to procedures commonly used for the preparation of cationic salts. For example, the free-acid form of A-32887 is dissolved in a suitable solvent such as acetone; a solution containing the stoichiometric quantity of the desired inorganic base in aqueous acetone is added to this solution. The salt thus formed can be isolated by routine methods, such as filtration or evaporation of the solvent.

The salts formed with organic amines can be prepared in a similar manner. For example, the gaseous or liquid amine can be added to a solution of A-32887 in a suitable solvent such as acetone; the solvent and excess amine can be removed by evaporation.

It is well known in the veterinary pharmaceutical art that the the form of an antibiotic is not ordinarily of great significance when treating an animal with the antibiotic. In most cases, conditions within the animal change the drug to a form other than that in which it was administered. The salt form in which it may be administered is, therefore, not of great significance. The salt form may, however, be chosen for reasons of economy, convenience, and toxicity.

A-32887 is produced by culturing an A-32887-producing strain of *Streptomyces albus* under submerged aerobic conditions in a suitable culture medium until substantial antibiotic activity is produced. A-32887 is separated from the culture medium by the use of various isolation and purification procedures understood in the art.

The new microorganism useful for the preparation of antibiotic A-32887 was isolated from a soil sample collected in Curacao in Dutch Antilles. This organism is classified as a strain of *Streptomyces albus* (Rossi-Doria) Waksman and Henrici. The characteristics upon which this classification is based are found in U.S. Pat. No. 4,133,876.

The *Streptomyces albus* culture useful for the production of antibiotic A-32887 has been deposited and made a part of the stock culture collection of the Northern Regional Research Center, Agricultural Research Service, U.S. Department of Agriculture, Peoria, Illinois 61604, from which it is available to the public under the number NRRL 11109.

The culture medium employed to grow *Streptomyces albus* NRRL 11109 can be any one of a number of media. For economy in production, optimal yield, and ease of product isolation, however, certain culture media are preferred. Thus, for example, a preferred carbohydrate source in large-scale fermentation in glucose, although dextrin, starch, maltose, and the like can also be used. A preferred nitrogen source is meat peptone, although other peptones, enzyme-hydrolyzed casein, soybean meal, amino acids and the like are also useful. Among the nutrient inorganic salts which can be incorporated in the culture media are the customary soluble salts capable of yielding iron, potassium, sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other substituents of the medium in amounts sufficient to meet the growth requirements of the organism. It may be necessary to add small amounts (i.e. 0.2 ml/l.) of an antifoam agent such as polypropylene glycol (M.W. about 2000) to large-scale fermentation media if foaming becomes a problem.

For production of substantial quantities of antibiotic A-32887, submerged aerobic fermentation in tanks is preferred. Small quantities of antibiotic A-32887 may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the vegetative inoculum can be the same as that employed for larger fermentations, but other media can also be employed.

The A-32877-producing organism can be grown at temperatures between about 22° and about 45° C. Optimum A-32887 production appears to occur at temperatures of about 30° C.

As is customary in aerobic submerged culture processes, sterile air is blown through the culture medium. For efficient production of antibiotic A-32887 the volume of air employed in tank productions is preferably about 0.25–0.5 volume of air per volume of culture medium per minute (V/V/M).

Production of antibiotic A-32887 can be followed during the fermentation by testing samples of the broth or of extracts of the mycelial solids for antibiotic activity against organisms known to be sensitive to this antibiotic. One assay organism useful in testing this antibiotic is *Bacillus subtilis* ATCC 6633. The bioassay is conveniently performed by paper-disc assay on agar plates.

Following its production under submerged aerobic fermentation conditions, antibiotic A-32887 can be recovered from the fermentation medium by methods employed in the fermentation art. Although the antibiotic activity produced during fermentation of the A-32887-producing organism occurs in both the broth and in the mycelial mass, the major part of the activity is in the filtered broth. Maximum recovery of antibiotic A-32887 is accomplished, therefore, by an initial filtration to separate the broth from the mycelial mass. The filtered broth can then be further purified to give antibiotic A-32887. A variety of techniques may be used in this purification. A preferred technique for purification of the filtered broth involves adjusting the broth to about pH 9 and extracting with a suitable solvent such as ethyl acetate. The extracting solvent can then be evaporated under vacuum to give partially-purified antibiotic A-32887. Further purification of A-32887 involves the use of chromatography. A preferred adsorbent for this purification is silica gel.

Alternatively, the culture solids, including medium constituents and mycelium can be used without extraction or separation, but preferably after removal of water, as a source of antibiotic A-32887. For example, after production of A-32887 antibiotic activity, the whole fermentation broth or the broth filtrate can be dried by lyophilization, by drum-drying, or by azeotropic distillation and drying. The dried whole broth or dried broth filtrate can then be mixed directly into feed premix.

Antibiotic A-32887 inhibits the growth of pathogenic bacteria, especially Gram-positive bacteria. Table I summarizes the minimal inhibitory concentrations (MIC), as measured by standard agar-dilution assays, at which A-32887 (Na-K salt) inhibits certain bacteria.

TABLE I

| Test Organism | MIC (mcg/ml) |
|---|---|
| *Staphylococcus aureus* 3055 | 6.25 |
| *Streptococcus faecalis* | 6.25 |
| *Staphylococcus sp.* | 1.56 |
| *Streptococcus sp.* | 3.12 |
| *Pasteurella multocida* (bovine) | 50.00 |
| *Pseudomonas sp.* | 3.12 |

The activity of A-32887 (Na-K salt) against illustrative bacteria, as measured by the conventional disc-diffusion method, is summarized in Table II.

TABLE II

| Test Organism | mcg/disc | Zone of Inhibition (mm) |
|---|---|---|
| Staphylococcus aureus 3055 | 300 | 15.6 |
| Staphylococcus aureus 3055 | 30 | 12.0 |
| Staphylococcus aureus 3074* | 300 | 16.0 |
| Staphylococcus aureus 3074* | 30 | 12.7 |
| Staphylococcus aureus 3130** | 300 | 15.2 |
| Staphylococcus aureus 3130** | 30 | 15.0 |
| Streptococcus pyogenes (Group A) | 300 | 17.5 |
| Streptococcus pyogenes (Group A) | 30 | 14.0 |
| Streptococcus sp. (Group D) | 300 | 14.7 |
| Streptococcus sp. (Group D) | 30 | 13.7 |
| Diplococcus pneumoniae | 300 | 18.0 |
| Diplococcus pneumoniae | 30 | 16.0 |

*Penicillin G-resistant
**Methicillin-resistant

The antimicrobial activity of two typical A-32887 acyl ester derivatives is compared with that of A-32887 (each as Na-K salts) in Table III. Activity against illustrative bacteria is measured by the conventional disc-diffusion method. In addition, the results of a conventional paper-disc agar-diffusion assay system (Plate Assay) against *Bacillus subtilis* ATCC 6633 are reported. The activity is this test is quantitated and uses a dried-broth reference standard which is assigned an arbitrary potency of 100 units/ml. The samples were assayed at 1 mg/ml.

TABLE III

| Compound | Plate Assay units/ml | Staphylococcus aureus | Bacillus subtilis | Micrococcus lutea | Bacillus subtilis* |
|---|---|---|---|---|---|
| A-32887 | 1350 | 16 | 18 | 16 | 30 |
| A-32887 Acetyl Ester Derivative | 238 | trace | 12 | trace | 22 |
| A-32887 n-Butyryl Ester Derivative | 1109 | 14 | 16 | 12 | 27 |

*Minimal media

The A-32887 compounds also inhibit the growth of anaerobic bacteria. Table IV summarizes the MIC's at which A-32887 (Na-K salt) inhibits various anaerobic bacteria, as determined by standard agar-dilution assay. End points were read after 24-hour incubation.

TABLE IV

| Test Organism | MIC (mcg/ml) |
|---|---|
| Actinomyces israelii | ≦ 0.5 |
| Clostridium perfringens | ≦ 0.5 |
| Clostridium septicum | ≦ 0.5 |
| Eubacterium aerofaciens | ≦ 0.5 |
| Peptococcus asaccharolyticus | ≦ 0.5 |
| Peptococcus prevoti | ≦ 0.5 |
| Peptostreptococcus anaerobius | ≦ 0.5 |
| Peptostreptococcus intermedius | 1.0 |
| Propionibacterium acnes | ≦ 0.5 |
| Bacteriodes fragilis ssp fragilis 111 | 2 |
| Bacteriodes fragilis ssp fragilis 1877 | 2 |
| Bacteriodes fragilis ssp fragilis 1936B | 2 |
| Bacteriodes fragilis ssp thetaiotaomicron | 2 |
| Bacteriodes melaninogenicus 1856/28 | 32 |
| Bacteriodes melaninogenicus 2736 | 2 |
| Bacteriodes vulgatis | 4 |
| Bacteriodes corrodens | 2 |
| Fusobacterium symbiosum | 32 |
| Fusobacterium necrophorum | 32 |

The activity of the A-32887 compounds against anaerobic bacteria, especially against *Clostridium perfringens*, suggests that the A-32887 compounds would be beneficial in the treatment or prevention of enteritis in chickens, swine, cattle, sheep, and goats and in the treatment or prevention of enterotoxemia in ruminants.

The acute toxicity of A-32887 (Na-K salt), when administered intraperitoneally to mice and expressed as $LD_{50}$, is 37.5 mg/kg×1.

The A-32887 compounds are useful in the treatment of swine dysentery. Treatment may be required to achieve either prevention and control of the disease. As used herein, "prevention" refers to treatment of uninfected, but susceptible, animals; and "control" refers to treatment of infected animals to minimize the severity of the disease. Thus, either infected or uninfected animals may be in need of treatment for the disease. Ordinarily, a lower concentration of active compound may be used to prevent the disease than is needed to control it. A preferred method of administration to swine is by incorporation of an appropriate amount of an A-32887 compound into the feed ration.

The reults of tests with A-32887 (Na-K salt) when administered to pigs infected with acute swine dysentery are reported in Table V. In this test, groups of four pigs were challenged orally with 5.0 ml of a colon-content/tissue suspension prepared from pigs suffering from acute swine dysentery. Treated pigs were challenged 24 hours after initiating feed treatment. The test was carried out over a period of 26 days, observing pigs daily, and weighing them weekly and on day 26.

TABLE V

| Treatment | Final Average Wt. per Pig (lbs) | No. Died per No. in Group | Diarrhea Index* | No. with Colon Lesions/No. in Group |
|---|---|---|---|---|
| A-32887 (Na-K salt) 100 g/ton | 30.3 | 0/4 | 22 | 2/4 |
| Infected Non-medicated Controls | 14.3 | 3/4 | 53 | 4/4 |
| Infected Non-medicated Controls | 14.8 | 2/4 | 52 | 4/4 |

*Fecal material for each group was rated daily with 0 = normal, 1 = slight blood or mucus, 2 = moderate blood or mucus, 3 = marked blood or mucus. Index is the total score per treatment for 25 days.

The A-32887 compounds are typically effective in the prevention and control of swine dysentery when administered to swine orally in feed in which an A-32887 compound is present in amounts of from about 50 to about 150 g/ton.

This invention also relates to feed compositions for swine that are either infected with or threatened by swine dysentery comprising swine ration and from about 50 to about 150 grams per ton of an A-32887 compound. A preferred method of administration is to mix the A-32887 compound with the animals' feed; however, it can be administered in other ways, for example, tablets, drenches, sustained-release boluses, or capsules. Formulation of these various dosage forms can be accomplished by methods well known in the veterinary pharmaceutical art. Each individual dosage unit should contain a quantity of A-32887 compound directly related to the proper daily dose for the animal to be treated.

In order to illustrate more fully the operation of this invention, the following examples are provided:

EXAMPLE 1

A Shake-flask Fermentation of A-32887

A lyophilized pellet of *Streptomyces albus* NRRL 11109 was dissolved in 1–2 ml of sterilized water. This solution was used to inoculate an agar slant having the following composition:

| Ingredient | Amount |
|---|---|
| Agar | 20 g |
| Dextrin | 10 g |
| Yeast extract | 1 g |
| Beef extract | 1 g |
| Enzymatic hydrolysate of casein* | 2 g |
| $CoCl_2 \cdot 6H_2O$ | 0.01 g |
| Deionized water | q.s. 1 liter |
| NaOH was added to raise the pH of the medium from about 6.2 to about 7.0, before sterilizing; pH after sterilization about 6.9. | |

*NZ Amine A, Humko Sheffield Chemical, Lyndhurst, N.J.

The inoculated slant was incubated at 30° C. for about 7 days. The mature slant culture was scraped with a sterile pipette or loop to loosen the spores. About one-fourth of the loosened spores were used to inoculate 50 ml of a vegetative medium having the following composition:

| Ingredient | Amount |
|---|---|
| Glucose | 15 g |
| Soybean meal | 15 g |
| Corn steep liquor | 10 g |
| NaCl | 5 g |
| $CaCO_3$ | 2 g |
| Cold tap water | q.s. 1 liter |
| The pH of this medium was adjusted from approximately 5.8 to about 6.5 by the addition of NaOH; post-sterilization pH about 6.5. | |

The inoculated vegetative medium was incubated in a 250-ml Erlenmeyer flask at 30° C. for about 48 hours on a shaker rotating through an arc two inches in diameter at 250 RPM.

This incubated vegetative medium (0.5–2.5 ml; 1–5%) was used to inoculate 50 ml of a production medium having the following composition:

| Ingredient | Amount (g/l.) |
|---|---|
| Glucose | 25.0 |
| Starch | 10.0 |
| Peptone* | 10.0 |
| Enzymatic-hydrolysate of casein | 4.0 |
| Blackstrap molasses | 5.0 |
| $MgSO_4 \cdot 7H_2O$ | 0.5 |
| $CaCO_3$ | 2.0 |
| Czapek's mineral stock*** | |
| Deionized water | q.s. 1 liter |

*Wilson's Peptone 159, Wilsons' Protein Technology
**NZ Amine A, Humko Sheffield Chemical, Lyndhurst, N.J.
***Czapek's mineral stock has the following composition: 100 g KCl; 100 g $MgSO_4 \cdot 7H_2O$; 2 g $FeSO_4 \cdot 7H_2O$; q.s. to 1 liter with deionized water The inoculated production medium was incubated in a 250-ml Erlenmeyer flask at 30° C. for about 2 to 3 days on a shaker rotating through an arc two inches in diameter at 250 RPM.

B. Tank Fermentation of A-32887

In order to provide a larger volume of inoculum, 20 ml of incubated vegetative medium, prepared as described in Section A, was used to inoculate 400 ml of a second-stage vegetative-growth medium having the same composition as that of the vegetative medium. This second-stage vegetative medium was incubated in a 2-liter flask for about 24 hours at 30° C. on a shaker rotating through an arc two inches in diameter at 250 RPM.

Incubated second-stage medium (800 ml) thus prepared was used to inoculate 100 liters of sterile production medium, prepared as described in Section A. The inoculated production medium was allowed to ferment in a 165-liter fermentation tank for 3 to 4 days at a temperature of 30° C. The fermentation medium was aerated with sterile air at the rate of 0.25 V/V/M and was stirred with conventional agitators at 250 RPM.

EXAMPLE 2

Separation of A-32887

Whole fermentation broth (925 l.), obtained by the method described in Example 1, was adjusted to pH 8.5 by the addition of NaOH, stirred for 45 minutes, and filtered with a filter aid (Hyflo Super-cel, a diatomaceous earth, Johns-Manville Products Corp.). The filtered cake was washed with water, and the water wash was added to the filtered broth. The filtered-broth solution was then extracted twice with ethyl acetate ($\frac{2}{3}$ volumes). The ethyl acetate extracts were combined and concentrated under vacuum to give an oily residue. The residue was dissolved in benzene (4 l.); the benzene solution was filtered; and the filtrate was applied to a 9.5 − × 162-cm silica-gel column (Grace, grade 62), prepared in benzene. After washing the column with benzene (24 l.), the eluting solvent was changed to benzene:ethyl acetate (3:2), collecting 37 liters consisting of fractions of 1 liter each. Elution was monitored by silica-gel thin-layer chromatography, using a benzene:ethyl acetate (1:1) solvent system and *Bacillus subtilis* bioautography for detection. The active fractions which contained A-32887 (11 l.) were combined and evaporated to dryness under vacuum. In order to remove color and other impurities, the residue thus obtained was dissolved in chloroform and chromatographed on a 2.2−×40-cm column of carbon (Pittsburgh 12×40), prepared in chloroform. The column was washed with chloroform (3 l.); the chloroform eluate was concentrated to dryness under vacuum. The residue thus obtained was dissolved in diethyl ether (200 ml). The resulting solution was evaporated slowly under vacuum to give a thick syrup. The syrup was slowly warmed, and n-hexane (500 ml) was added with stirring. This solution was allowed to stand at room temperature until the A-32887 had crystallized. The crystalline A-32887 was separated by filtration and dried. The A-32887 was recrystallized by dissolving in acetone (500 ml), slowly adding water (200 ml), and allowing the resulting solution to stand at room temperature. The recrystallized A-32887 was separated by filtration, washed with water and dried to give 59 g of A-32887 Na-K salt. Further recrystallization gave additional A-32287 (Na-K salt) in the following amounts: 8.4 g in the second crop, and 5.2 g in the third crop (mp 158°–160°).

EXAMPLE 3

Preparation of A-32887 Free Acid

A-32887 Na-K salt (1 g), obtained as described in Example 2, was dissolved in dioxane (200 ml). Water (25 ml) was added to this solution; the resulting solution was adjusted to pH 3 by the addition of dilute HCl. The acidified solution was stirred, and maintained at pH 3 with HCl, as water (100 ml) was slowly added. The resulting solution was evaporated under vacuum to remove the dioxane; the resulting aqueous suspension was extracted twice with ethyl acetate (equal volumes). The combined ethyl acetate extract was evaporated under vacuum to give an oily residue. This residue was dissolved in chloroform and re-evaporated under vacuum to give A-32887 free acid as a white amorphous powder (524 mg; mp about 90° C.)

EXAMPLE 4

Preparation of A-32887 Silver Salt

A-32887 Na-K salt (200 mg), obtained was described in Example 2, was dissolved in methanol (10 ml). An aqueous solution of silver nitrate (2 ml; 50 mg/ml) was added slowly. The resulting solution was placed in a beaker wrapped with aluminum foil to prevent degradation (reduction) of the silver. The solution was kept at 5° C. until crystallization was complete. The crystals were separated by filtration and were recrystallized from n-hexane to give A-32887 silver salt as very fine white needles (mp 166°–168° C.).

EXAMPLE 5

Preparation of the Sodium Salt of A-32887

A-32887 free acid (500 mg), prepared as described in Example 3, was dissolved in acetone (150 ml); water (20 ml) was added. The resulting mixture was adjusted to pH 9 with NaOH. Water (200 ml) was then added, and the resulting solution was stirred for ½ hour. The solution was concentrated under vacuum to remove acetone. The resulting suspension was extracted with an equal volume of ethyl acetate. The ethyl acetate extract was concentrated under vacuum to dryness. The residue was dissolved in warm acetone (20 ml); water was added until the solution was turbid; and the solution was then allowed to crystallize. The crystals were removed by filtration, washed with water, and dried to give 306 mg of A-32887 sodium salt (mp 130°–133° C.).

EXAMPLE 6

Preparation of the Methyl Ether Derivative of A-32887

A-32887 free acid (3 g), prepared as described in Example 3, was dissolved in methanol (300 ml) and allowed to stand at room temperature for 12 hours. The conversion was monitored by silica-gel TLC, using a benzene:ethyl acetate (1:1) solvent system and $H_2SO_4$ spray for detection. The solution was evaporated to dryness under vacuum. The residue obtained was dissolved in benzene (40 ml). This solution was applied to a 3.2−×95-cm column of silica gel (Grace, grade 62), packed in benzene. The column was eluted with benzene:ethyl acetate (3:2), collecting 25-ml fractions, and monitoring elution by TLC. Fractions 90–220, which contained most of the desired product, were combined and evaporated under vacuum to dryness. The residue, dissolved in benzene (15 ml) was rechromatographed on a 1.8−×112-cm column of silica gel (Grace, grade 62), prepared in benzene. The column was eluted with benzene:ethyl acetate (9:1), collecting 25-ml fractions and monitoring elution by TLC. At fraction 383, the eluting solvent was changed to benzene:ethyl acetate (4:1); and at fraction 780 the solvent was changed to benzene:ethyl acetate (7:3). Fractions 450–700 contained A-32887; fractions 702–760 contained a mixture of A-32887 and A-32887 methyl ether derivative; and fractions 761–1130 contained A-32887 methyl ether derivative. Fractions 761–1130 were combined and evaporated to dryness under vacuum. The residue was dissolved in ethyl acetate (20 ml); n-hexane (80 ml) was added; and the solution was allowed to crystallize. The crystals were removed by filtration and dried to give 242 mg of A-32887 methyl ether derivative as the sodium salt (mp 214°–216° C.).

EXAMPLE 7

Preparation of the Acetyl Ester Derivative of A-32887

A-32887 Na-K salt (200 mg), prepared as described in Example 2, was dissolved in pyridine (8 ml); acetic anhydride (3.2 ml) was added. The mixture was allowed to stand overnight and then was evaporated under vacuum to dryness. The residue was dissolved in t-butanol and lyophilized to give 231 mg of the acetyl ester derivative of A-32887 (Na-K salt) as a white amorphous powder, mp 127°–129° C.

EXAMPLE 8

Preparation of the n-Butyryl Ester Derivative of A-32887

A-32887 (Na-K salt; 200 mg) was dissolved in pyridine (14 ml), and n-butyric anhydride (14 ml) was added. The mixture was allowed to stand for 17 hours at room temperature; water (14 ml) was added; and the solution was then concentrated to an oil in vacuo. The oily residue was lyophilized from dioxane-water several times to give 240 mg of the n-butyryl ester derivative of A-32887 (Na-K salt) as a white amorphous powder, mp 59°–62° C.

EXAMPLE 9

A-32887-Improved Swine Ration

A balanced swine ration is prepared as follows:

| Ingredient | % | lbs./ton |
|---|---|---|
| Corn, Yellow, Ground | 73.15 | 1463 |
| Soybean Oil Meal, Solvent Extracted, Dehulled, 50% | 12.30 | 246 |
| Alfalfa Meal, Dehydrated, 17% | 2.50 | 50 |
| Meat Scraps, 55% | 2.50 | 50 |
| Fish Meal | 2.50 | 50 |
| Distiller Dried Solubles (Corn) | 2.50 | 50 |
| Animal Fat | 2.00 | 40 |
| Calcium Carbonate | 0.70 | 14 |
| Dicalcium Phosphate, Feed Grade | 0.50 | 10 |
| NaCl | 0.50 | 10 |
| Swine Vitamin Premix[1] | 0.50 | 10 |
| Methionine Hydroxy Analog, 93% | 0.20 | 4 |
| Trace Mineral Premix[2] | 0.10 | 2 |
| Selenium Premix[3] | 0.05 | 1 |
| Total | 100.00 | 2000 |

[1]Each kg of premix contains the following: 77,161 IU Vitamin $D_2$; 2,205 IU Vitamin E; 411 mg riboflavin; 1,620 mg pantothenic acid; 2,205 mg niacin; 4.4 mg Vitamin $B_{12}$; 441 mg Vitamin K; 19,180 mg choline; 110 mg folic acid; 165 mg pyridoxine; 110 mg thiamine; 22 mg biotin.

[2]Each kg of premix contains the following: 50 g manganese as manganese sulfate; 100 g zinc as zinc carbonate; 50 g iron as ferrous sulfate; 5 g copper as copper oxide; 1.5 g iodine as potassium iodide and 150 g maximum and 130 g minimum calcium as calcium carbonate.

[3]Each kg of premix contains 200 mg of selenium as sodium selenite.

A-32887 (Na-K salt; 100 g) is mixed with from about 5 to about 10 lbs. of soybean mill run to give a feed premix. From 5–10 lbs of this A-32887 premix is thoroughly mixed with a sufficient amount of the above-described swine ration to give a concentration of 100 g of A-32887 per ton of ration. Swine fed such a ration, with water ad libitum, are protected against the lethal effects of swine dysentery.

We claim:

1. A method of treating dysentery in swine which comprises orally administering to swine in need of said treatment an effective amount of a compound selected from the group consisting of (1) antibiotic A-32887 which has the following structure:

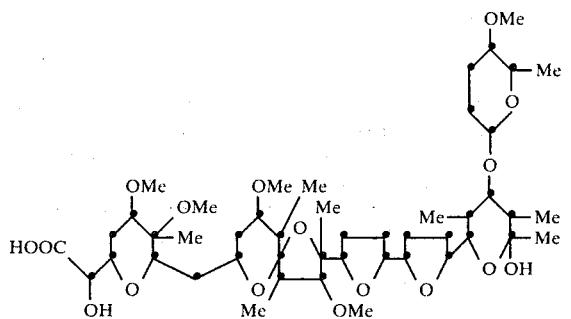

(2) the acetyl ester derivative of A-32887, which has an approximate empirical formula of $C_{50-51}H_{82-88}O_{18-19}$, and which in its Na-K salt form has a molecular weight of about 988, a melting point of about 127°–129° C., and an approximate $R_f$ value of 0.40 on silica-gel TLC in benzene:ethyl acetate (1:1), and an infrared absorption spectrum as shown in FIG. 4 of the drawings; (3) the n-butyryl ester derivative of A-32887 which has an approximate empirical formula of $C_{52-53}H_{86-92}O_{18-19}$, and which in its Na-K salt form has a molecular weight of about 1016, a melting point of about 59°–62° C., an approximate $R_f$ value of 0.64 on silica-gel TLC in benzene:ethyl acetate (1:1), and an infrared absorption spectrum as shown in FIG. 5 of the drawings; and (4) the pharmaceutically-acceptable salts of antibiotic A-32887 and of the acetyl and n-butyryl ester derivatives of antibiotic A-32887.

2. The method of claim 1 wherein the compound is antibiotic A-32887 or a pharmaceutically-acceptable salt thereof.

3. The method of claim 2 wherein the compound is antibiotic A-32887 Na-K salt.

4. A method of treating dysentery in swine which comprises orally administering to swine an effective amount of a compound selected from the group consisting of (1) the methyl ether derivative of A-32887 which has a molecular weight of about 960 and an approximate empirical formula of $C_{49-50}H_{82-88}O_{17-18}$, and which in its sodium salt form is a white crystalline compound, when crystallized from n-hexane:ethyl acetate, having a melting point of about 214°–216° C. and having the following characteristics:

(a) a molecular weight of about 982, as determined by FD mass spectrometry;

(b) an infrared absorption spectrum in chloroform with significant absorption maxima at the following frequencies (cm$^{-1}$): 3400 (broad), 2990, 2960, 2930, 2870, 2820, 1725, 1610, 1455, 1407, 1370, 1309, 1282, 1240, 1180, 1158, 1110, 1093, 1082, 1057, 1010, 980, 945, 900, 868, 858, 827, 802, 700, and 653;

(c) a proton-magnetic-resonance spectrum which indicates the presence of six methoxyl groups;

(d) a specific rotation as follows: $[\alpha]_D^{25} - 5.1°$ (c 1, $CHCl_3$);

(e) an X-ray powder diffraction pattern (CuNi, 1.5405λ, d = interplanar spacing in angstroms) as follows:

| d | Relative Intensity |
|---|---|
| 13.18 | 50 |
| 12.01 | 50 |
| 9.02 | 100 |
| 8.26 | 100 |
| 7.19 | 80 |
| 6.46 | 50 |
| 5.78 | 20 |
| 5.46 | 20 |
| 5.00 | 30 |
| 4.24 | 20 |
| 3.72 | 20 |
| 3.36 | 05 |

(f) a titratable group in 80% aqueous dimethylformamide with a $pK_a$ value of about 5.4;

(g) solubility in methanol, ethanol, dimethylformamide, dimethyl sulfoxide, ethyl acetate, chloroform, acetone, and benzene; slight solubility in hexane and heptane; and insolubility in water;

(h) an acid function capable of forming salts and ester derivatives; and (2) the pharmaceutically-acceptable salts thereof.

5. The method of claim 4 wherein the compound is A-32887 methyl ether derivative sodium salt.

6. A feed adapted to treat swine dysentery comprising swine ration and from about 50 to about 150 grams per ton of a compound selected from the acetyl ester derivative of A-32887 and the n-butyryl ester derivative of A-32887 as defined in claim 1; the methyl ether derivative of A-32887 as defined in claim 4; and the pharmaceutically acceptable salts of each of these.

7. A feed of claim 6 wherein the compound is the acetyl ester derivative of A-32887 or a pharmaceutically acceptable salt thereof.

8. A feed of claim 6 wherein the compound is the n-butyryl ester derivative of A-32887 or a pharmaceutically acceptable salt thereof.

9. A feed of claim 6 wherein the compound is the methyl ether derivative of A-32887 or a pharmaceutically acceptable salt thereof.

* * * * *

UNITED STATES PATENT AND TRADEMARK OFFICE
CERTIFICATE OF CORRECTION

PATENT NO. : 4,331,658

DATED : May 25, 1982

INVENTOR(S) : Robert L. Hamill and Marvin M. Hoehn

It is certified that error appears in the above—identified patent and that said Letters Patent is hereby corrected as shown below:

Column 1, lines 43-49, that portion of the structural formula reading

" 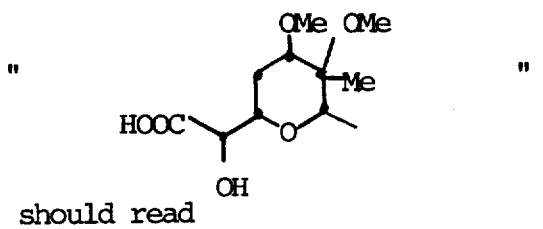 "

should read

-- 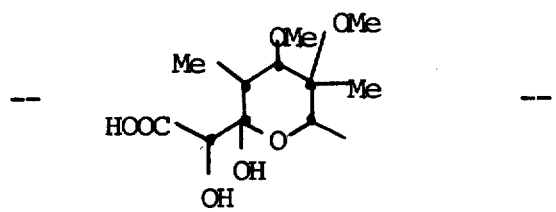 --

Column 15, lines 46-51, that portion of the structural formula reading

" 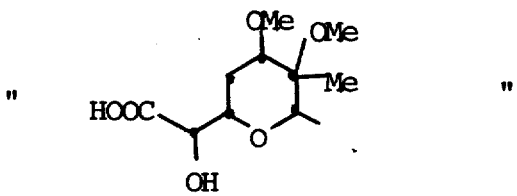 "

UNITED STATES PATENT AND TRADEMARK OFFICE
CERTIFICATE OF CORRECTION

PATENT NO. : 4,331,658  Page 2 of 2

DATED : May 25, 1982

INVENTOR(S) : Robert L. Hamill and Marvin M. Hoehn

It is certified that error appears in the above—identified patent and that said Letters Patent is hereby corrected as shown below:

should read

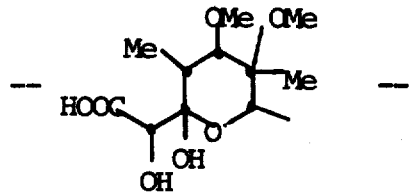

[SEAL]

Signed and Sealed this

Second Day of August 1983

Attest:

Attesting Officer

GERALD J. MOSSINGHOFF

Commissioner of Patents and Trademarks